United States Patent [19]

Williams

[11] Patent Number: Plant 5,357

[45] Date of Patent: Nov. 27, 1984

[54] MINIATURE ROSE PLANT—MINCCO

[76] Inventor: Ernest D. Williams, 1510 Lebanon Ave., Dallas, Tex. 75208

[21] Appl. No.: 491,762

[22] Filed: May 5, 1983

[51] Int. Cl.[3] ..... A01H 5/00

[52] U.S. Cl. ..... Plt./7

[58] Field of Search ..... Plt./77

*Primary Examiner*—Robert E. Bagwill

[57] ABSTRACT

The subject of the present disclosure is a new and distinct variety of miniature rose plant characterized by the pink and white bi-color coloration of the very double flowers and by the profusion of bloom.

1 Drawing Figure

1

The present invention relates to a new and distinct variety of hardy, dwarf, bush type rose plant of the miniature class; the variety being primarily characterized—as to novelty—by the pink and white bi-color coloration of the flowers which in general color effect are similar to Toy Clown (miniature—U.S. Plant Pat. No. 2,909).

The variety is further characterized by:

An abundance of bloom, with flowers usually borne singly.

Slight fragrance.

A plant which is vigorous, of bushy upright shape with semi-glossy to glossy, small foliage, with pointed leaflets; the buds and flowers being similar in form and size to Toy Clown (miniature—U.S. Plant Pat. No. 2,909), but averaging more petals.

The plant, which has a normal height of about 30 cm or more, can easily be maintained at lesser height by occasional trimming.

A plant which grows and blooms satisfactorily outdoors; is good for growing in pots; and provides excellent garden decoration as well as cut flowers.

The present variety of miniature rose was originationed by me at my nursery located at Dallas, Tex., under conditions of careful control and observation, as a cross between Little Darling (a floridunba—U.S. Plant Pat. No. 1,581, expired) as the seed parent and Over The Rainbow (miniature—U.S. Plant Pat. No. 3,472) as the pollen parent.

Subsequent to origination of the variety I successfully reproduced it, at my nursery located as aforesaid, by cuttings; the reproductions having run true in all respects.

The color photograph illustrates the variety, including the foliage, bud and flower.

Referring now specifically to the new and distinct variety of miniature rose plant, the following is a detailed description thereof in outline; all major color plate identification being by reference to the British Colour Council Horticultural Color Chart, except where common terms of color definition are employed.

Type: Hardy; dwarf; bushy; upright; seedling; outdoors; cut flowers; garden decoration; potted plant.

Class: Miniature. Variety identification: Mincco, Commercial Synonym: Peggy's Delight.

Flowers borne: Usually singly on slender wirey stems.

Quantity of bloom: Abundant.

Bud:

2

*Peduncle.*—Medium to long length; slender but sturdy; erect; medium green, sometimes tinted bronze (outdoors); hairs — few.

*Before calyx breaks.*—Size — small. Form short; pointed with several foliaceous appendages and few or no tiny hairs on surface of bud; with foliaceous parts extending beyond the tip of the bud equal to one-half or less of its length. Color — medium green, occasionally tinted with bronze (outdoors).

*As calyx breaks.*—Color — near white, often tinted reddish near tip.

*Opening.*—Opens well in all weather.

Bloom:

*Size when fully open.*—Small, averaging about 35–40 mm (1½"). Petalage very double — averaging about 45 to 50 petals, arranged regularly plus sometimes several small petaloids. Form — high centered, with petals reflexing loosely outward, and later at maturity, rolled loosely outward and downward. Open flowers usually show no stamens.

Petals: Fairly thick; satiny on inside and on outside surface.

*Shape.*—Outside petals, broad lanceolate — almost round; intermediate — broad lanceolate with small acute tip; intermediate — lanceolate with short acute tip.

Color: Newly opened flower from a plant grown outdoors (1982 season), Dallas, Tex.:

*Outside petal.*—Outside surface — near white on basal one-half of petal shading or blending into a soft pink near petal edges. Inside surface — near Tyrian Rose 24 to Tyrian Rose 24/2 (or similar) with white to near white area on basal ⅓ of petal.

*Intermediate petal.*—Outside surface — similar to outside petal. Inside surface — similar to outside petal.

*Inner petal.*—Outside surface — same as intermediate petal; inside surface — same as intermediate petal.

*General color effect.*—Newly opened flowers — deep pink. Three days open — color similar to newly opened flowers but less brilliant.

*Behavior.*—Opens well in all weather. Color becomes less brilliant as flowers age.

*Flower longevity* (*May* 1982).—Plant in pot 6–8 days or longer. Cut flowers at living room temperature 4–5 days or longer.

Reproductive organs:

*Stamens.*—Few or none.

*Filaments.*—Varying length, yellow.

*Anthers.*—Yellow (if present).

*Pollen.*—Usually none.

*Pistils.*—Average number.

*Styles.*—Fairly even; medium to short length; bunched; color — pale greenish.

*Ovaries.*—All enclosed in calyx.

*Hips.*—None.

*Sepals.*—Permanent; spear shaped; recurved against peduncle.

*Seed.*—None.

Foliage:

*Leaves.*—Compound of five (sometimes three or seven) leaflets; fairly small; leathery; semi-glossy to matt.

*Leaflets.*—Shape: broad, nearly oval, apex acute base rounded or rounded acute. Margin serrate. Color: medium to dark green; new growth — normal (medium) green — often tinted reddish. Rachis: medium strength; upper side may have a few tiny short prickles or hairs, grooved; underside sparsely thorny with few or no tiny prickles. Stipules: medium long; narrow to medium width; medium length, narrow points which turn out usually at about 45 degrees or less.

Growth:

*Habit.*—Dwarf; bushy; upright; much branched.

*Growth.*—Free vigorous, internodes short.

*Canes.*—Medium; slender; sturdy.

*Main stems.*—Color: medium green.

*Thorns.*—Few; slender, hooked slightly downward; color; tan. Prickles — none. Hairs — none.

*Branches.*—Color: medium green. Thorns: few; medium length; slender; nearly straight, inclined downward. Medium oval base. Prickles: none. Hairs: none.

The miniature rose plant and its flowers as herein described may vary in slight detail due to climatic, soil and cultural conditions under which the variety may be grown; the present description being of the variety as grown at Dallas, Tex.

The following is claimed:

1. A new and distinct variety of miniature rose plant of hardy, dwarf, bushy, upright, much branched habit, substantially as illustrated and described, characterized by buds and flowers of a deep pink and white bi-color, being of a shade generally near Tyrian Rose 24 to Tyrian Rose 24/2 (or similar), on the top surface and near white on reverse, the bud and flower resembling the variety Toy Clown (Plant Pat. No. 2,909) in form and size but having more petals; and further characterized by a plant of vigorous and compact growth habit, easy to propagate from cuttings, with an abundance of flowers borne usually one to the stem.

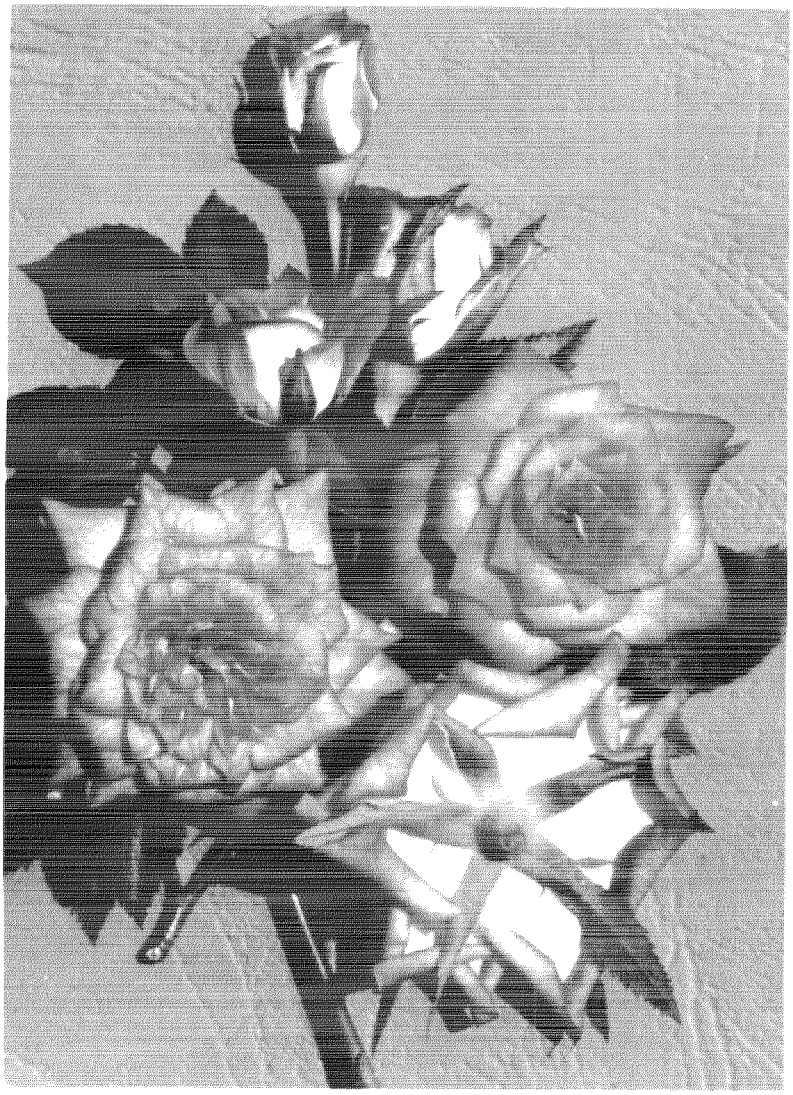

* * * * *